(12) United States Patent
Conger et al.

(10) Patent No.: US 9,421,360 B2
(45) Date of Patent: Aug. 23, 2016

(54) MEDICAL DEVICE LEAD ASSEMBLY HAVING INTEGRATED PRESSURE-RESISTING MEMBER

(71) Applicant: PACESETTER, INC., Sylmar, CA (US)

(72) Inventors: Steven R. Conger, Agua Dulce, CA (US); Michael Childers, Montrose, CA (US); Yoheng Hanson Chang, Arcadia, CA (US); Tyler Strang, Valencia, CA (US); John R. Helland, Tallahassee, FL (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 14/056,860

(22) Filed: Oct. 17, 2013

(65) Prior Publication Data

US 2015/0112414 A1    Apr. 23, 2015

(51) Int. Cl.
*A61N 1/05* (2006.01)
(52) U.S. Cl.
CPC ............... *A61N 1/05* (2013.01); *A61N 1/0558* (2013.01); *A61N 2001/0582* (2013.01)

(58) Field of Classification Search
CPC ....... A61N 1/05; A61N 1/0558; A61N 1/057; A61N 2001/0582
USPC .................................................. 607/116, 122
See application file for complete search history.

(56) References Cited

U.S. PATENT DOCUMENTS

| 5,968,087 | A | * | 10/1999 | Hess et al. ............. 607/127 |
| 2004/0199233 | A1 | * | 10/2004 | Rodriguez ............ A61N 1/05 607/116 |
| 2010/0228331 | A1 | | 9/2010 | Conger |

* cited by examiner

*Primary Examiner* — Joseph Dietrich

(57) ABSTRACT

A medical device configured to be secured to an individual may include a housing containing one or more electrical components, and one or more leads electrically connected to the housing. Each lead may include an insulating jacket that surrounds a central core including one or more conductors, and at least one pressure-resisting member integrally formed with one or both of the insulating jacket or the central core. The pressure-resisting member is configured to resist one or more forces exerted into the central core. For example, the pressure-resisting member may include one or more of a suture-anchoring member or a lead-strengthening member.

17 Claims, 12 Drawing Sheets

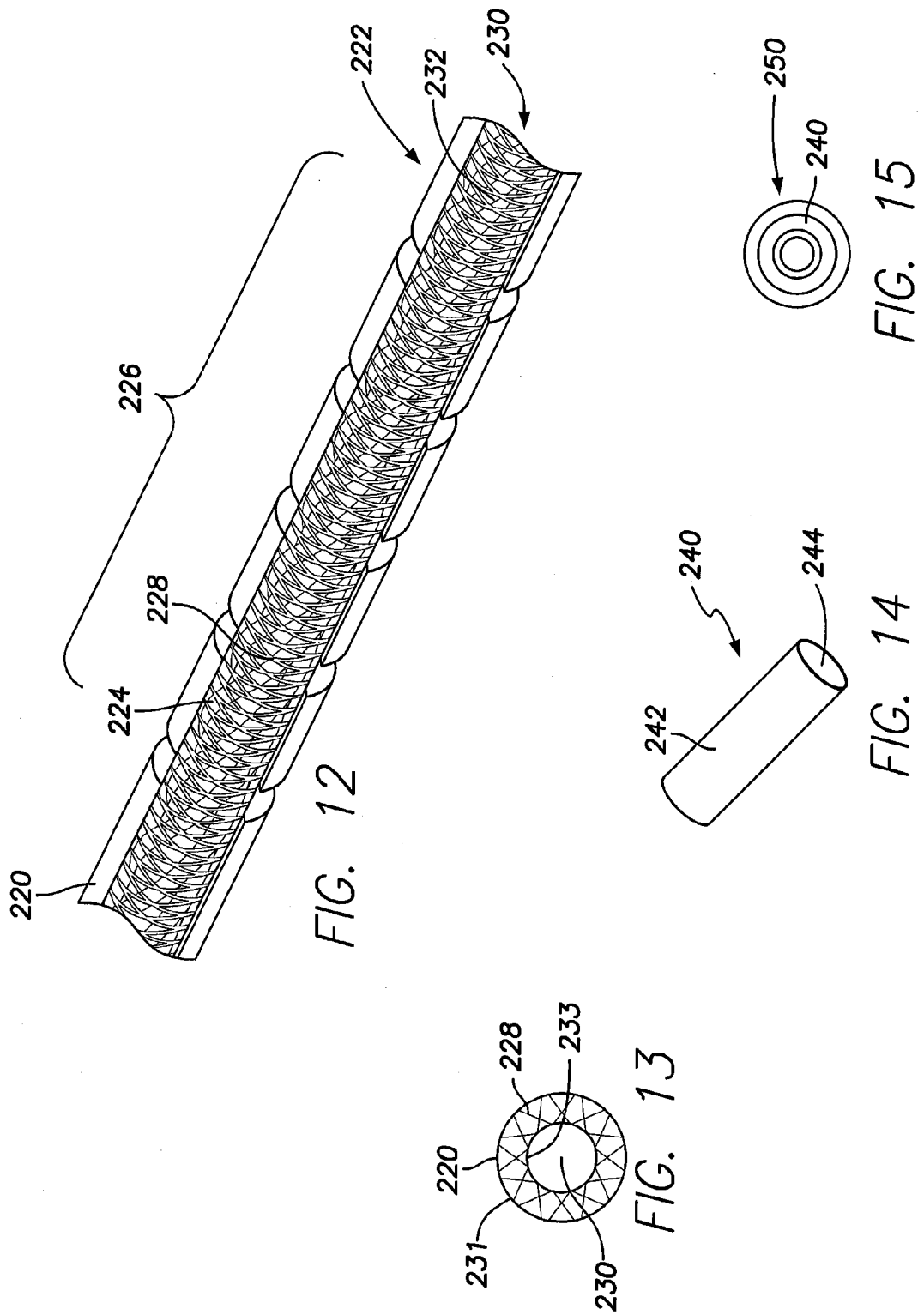

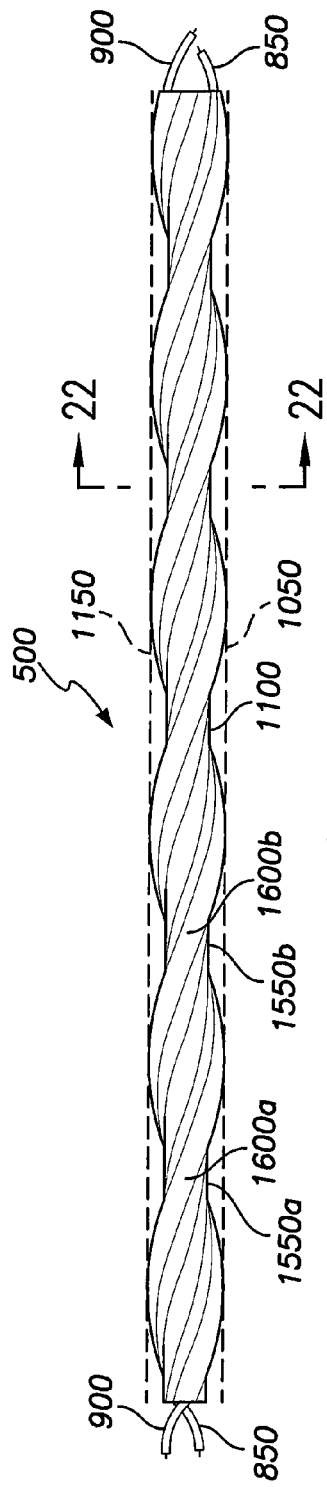
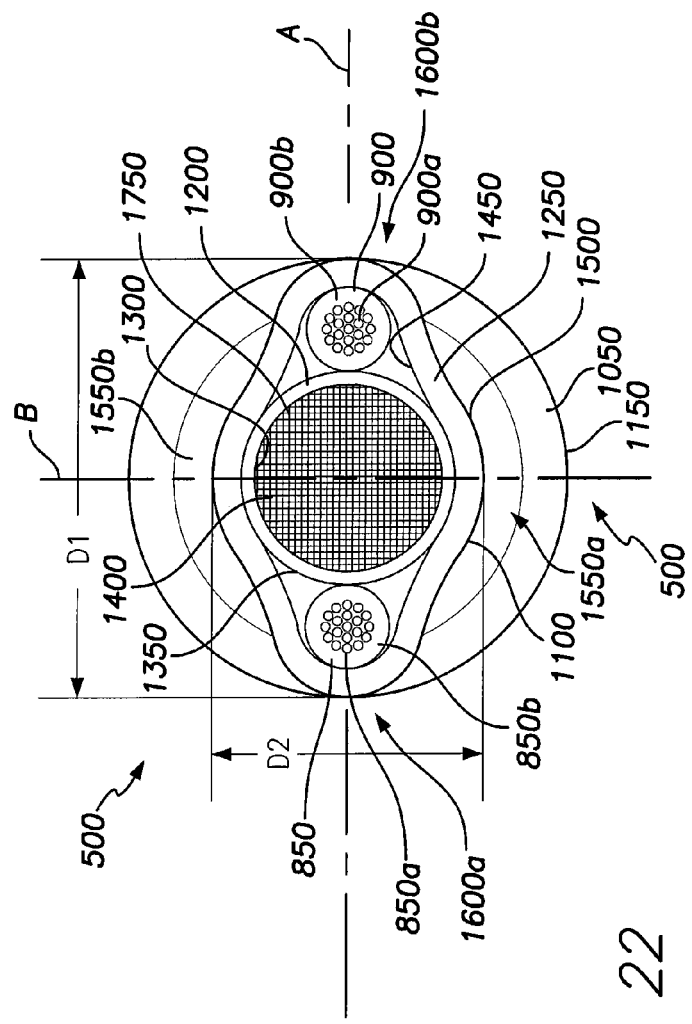

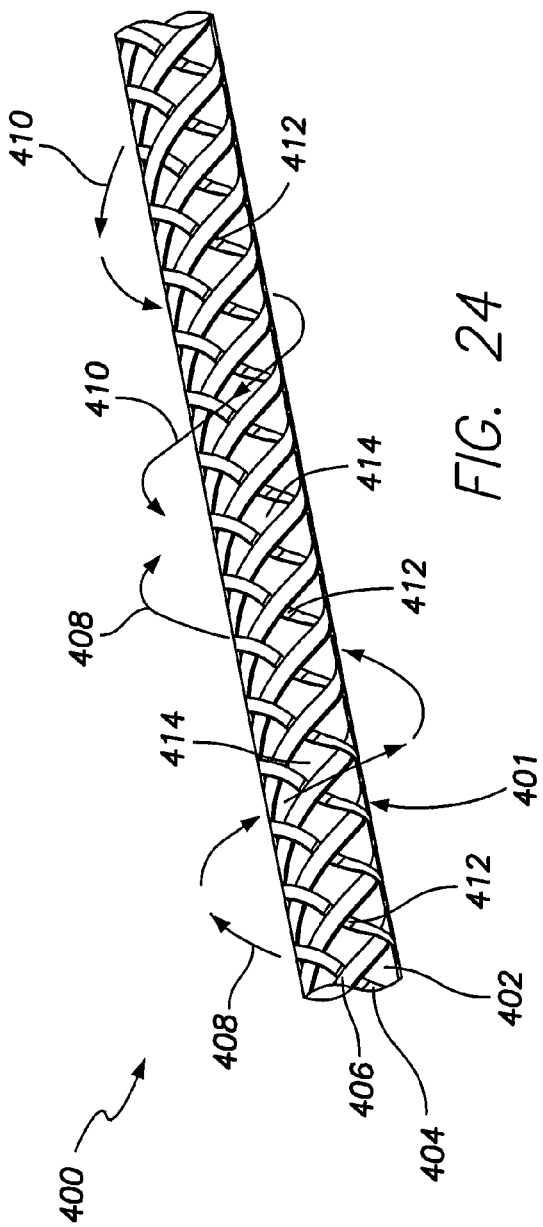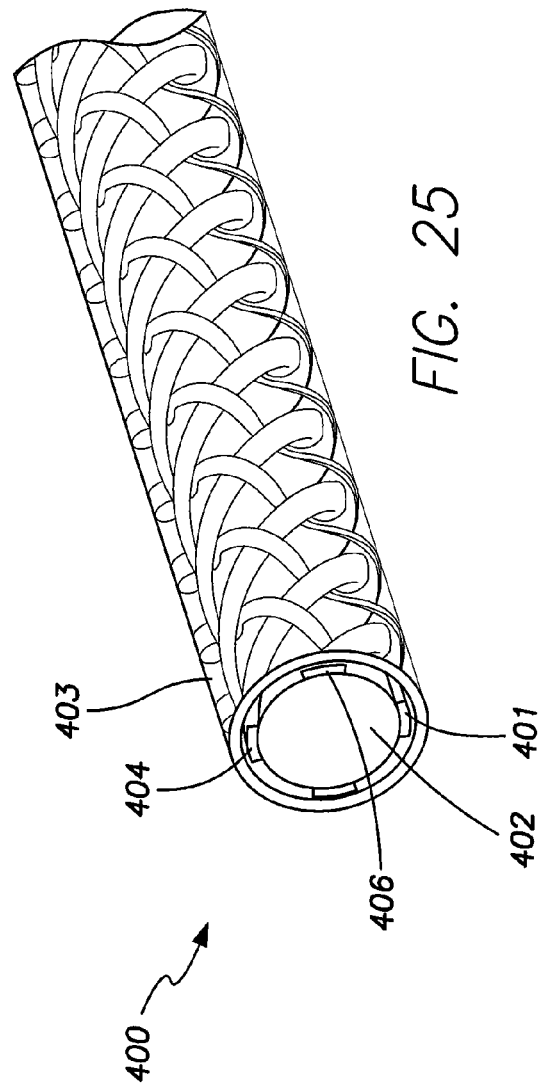

MEDICAL DEVICE LEAD ASSEMBLY HAVING INTEGRATED PRESSURE-RESISTING MEMBER

FIELD OF THE INVENTION

Embodiments of the present disclosure generally relate to medical device leads, and, more particularly, to medical device leads having one or more integrated pressure-resisting members, such as suture-anchoring members and/or lead-strengthening members.

BACKGROUND OF THE INVENTION

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RF") ablation systems, and the like. Implantable medical devices (hereafter generally "implantable medical devices" or "IMDs") are configured to be implanted within patient anatomy and commonly employ one or more leads with electrodes that either receive or deliver voltage, current or other electromagnetic pulses (generally "energy") from or to an organ or tissue (collectively hereafter "tissue") for diagnostic or therapeutic purposes.

Typically, each lead of a medical device is securely anchored to a portion of patient tissue through sutures. Separate and distinct suture sleeves are generally slid over the leads to suitable areas for anchoring to the patient tissue. Once a suture sleeve is positioned at a desired area, a medical professional, such as a surgeon, securely connects the sutures to the patient tissue and ties the ends of the sutures around the suture sleeve.

The suture sleeve protects the lead from being damaged. For example, if no suture sleeve were used, the force of tying the suture around the lead could crush or otherwise damage the conductors within the lead. The suture sleeve protects the lead from the compressive or crushing force exerted by the suture tie. Also, the suture sleeve is intended to grip an outer surface of the lead with sufficient traction to prevent the lead from slipping or otherwise moving within the suture sleeve. However, it has been found that in certain instances leads may be susceptible to slipping within the suture sleeve. Lead slippage within the suture sleeve typically dislodges the lead from an anchoring site, and may result in loss of therapy. Additional surgery is then needed to reposition and anchor the lead.

Because of the possibility of lead slippage within a suture sleeve, many medical professionals prefer to tie the sutures to the suture sleeves with an excessive amount of force. In doing so, however, the increased force of the suture ties may pinch the lead body, and damage the underlying components of the lead. Indeed, with enough force, the suture sleeve itself may even split open.

Further, because the suture sleeves are separate and distinct components from the leads themselves, the suture sleeves are manufactured separately and distinctly from the lead body, thereby adding to the cost of the lead and device assembly. Also, as noted above, during surgery, before anchoring the leads to patient tissue, a surgeon first must slide the suture sleeves over the leads, and then position each suture sleeve to a desired position, thereby adding to the duration of the procedure. Accordingly, the use of suture sleeves generally leads to increased manufacturing and surgical time and cost.

Additionally, leads often fail due to abrasion. For example, a lead may rub against a device, such as a can of an implantable medical device, another lead, calcified patient tissue, or the like. Further, the lead itself may be pinched between a device and patient anatomy, or even between patient anatomy, such as between bones proximate to a collar bone and/or shoulder of an individual. The pinching may crush or otherwise damage components of the lead.

In order to protect against the harmful effects of lead abrasion or crushing, some leads are manufactured with additional layers of material. However, with each additional layer of material, the leads become stiffer. With increased stiffness, the lead body may be difficult to articulate and navigate through patient anatomy. Moreover, a stiff lead may damage patient anatomy. For example, a stiff lead may perforate vasculature.

SUMMARY

Certain embodiments of the present disclosure provide a medical device configured to be secured to an individual. The medical device may include a housing containing one or more electrical components, and one or more leads electrically connected to the housing. Each lead may include an insulating jacket that surrounds a central core including one or more conductors, and at least one pressure-resisting member integrally formed with one or both of the insulating jacket or the central core. The pressure-resisting member(s) is configured to resist one or more forces exerted into the central core. The pressure that the pressure-resisting member(s) resists may be various types of pressure, such as crushing and abrading pressures, or the pressure exerted by a suture tie into the lead.

In at least one embodiment, the pressure-resisting member(s) may include at least one suture-anchoring member integrally formed with one or both of the insulating jacket or the central core. The suture-anchoring member(s) may include at least one feature that is configured to retain at least a portion of suture material that is configured to securely anchor the lead(s) to tissue of the individual.

In at least one embodiment, the feature(s) may include one or more grooves formed on an outer surface of the insulating jacket configured to allow the portion of suture material to nest therein. The grooves may be coaxial circular grooves. Alternatively, the feature may include a single helical groove that spirals around at least a portion of the insulating jacket.

Alternatively, the feature(s) may include one or more rims radially extending from an outer surface of the insulating jacket. The rim(s) may include at least two coaxial rims separated by a suture-nesting area. Optionally, a single helical rim may spiral around at least a portion of the insulating jacket.

In at least one embodiment, the suture-anchoring member(s) may include one or more of a hook, barb, clasp, or tab.

The suture-anchoring member(s) may include a thickened wall portion configured to resist compressive force. The suture-anchoring member(s) may include at least one jacket-supporting member contained within or bonded to the insulating jacket. The jacket-supporting member(s) may include wire mesh. Optionally, the jacket-supporting member(s) may include a cylindrical sleeve, wherein the cylindrical sleeve provides rigidity to the at least one jacket-supporting member. The jacket-supporting member(s) may include one or more channels, wherein the one or more channels provide flexibility to the at least one jacket-supporting member.

The suture-anchoring member(s) may extend over at least a proximal portion of the insulating jacket. A plurality of suture-anchoring members may be regularly spaced over a portion the insulating jacket. In at least one embodiment, the suture-anchoring member(s) may extend over an entire length of the insulating jacket.

The pressure-resisting member(s) may include at least one lead-strengthening member integrally formed with one or both of the insulating jacket or the central core. The pressure-resisting member(s) may be configured to resist abrasive or crushing forces exerted by one or more of the housing, another lead, or patient anatomy. The lead-strengthening member(s) may include one or more fibers extending along the central core. For example, two fibers may be spirally-wound around the central core to form a lattice.

The conductors may include first and second helically-routed conductors. Optionally, the conductors may include more than two helically-routed conductors. For example, the conductors may include three, four, five, six, or more helically-routed conductors. The medical device may include an implantable pacemaker, an implantable cardioverter-defibrillator, an internal or external neurostimulation device, or a Holter monitor, for example.

BRIEF DESCRIPTION OF THE DRAWINGS

FIG. 12 illustrates an isometric internal view of an insulating jacket of a lead, according to an embodiment of the present disclosure.

FIG. 13 illustrates an axial cross-sectional view of an insulating jacket, according to an embodiment of the present disclosure.

FIG. 14 illustrates an isometric view of a jacket-supporting member, according to an embodiment of the present disclosure.

FIG. 15 illustrates an axial cross-sectional view of an insulating jacket, according to an embodiment of the present disclosure.

FIG. 21 illustrates a longitudinal side view of the lead of FIG. 20 with the insulating jacket shown in phantom lines to reveal a helical core assembly, according to an embodiment of the present disclosure.

FIG. 22 illustrates a transverse cross-section of the lead as taken along section line 22-22 of FIG. 21, according to an embodiment of the present disclosure.

FIG. 24 illustrates an isometric view of a lead-strengthening member integrally formed with a lead, according to an embodiment of the present disclosure.

FIG. 25 illustrates an isometric partial-internal view of a lead-strengthening member integrally formed with a lead, according to an embodiment of the present disclosure.

DETAILED DESCRIPTION

Embodiments of the present disclosure provide a medical device having one or more leads, each of which may include one or more integral pressure-resisting members, such as an integral suture-anchoring member, and/or a lead-strengthening member. The pressure resisting members, such as suture-anchoring members and/or lead-strengthening members, may be integrally formed and/or molded with the lead(s). For example, the suture-anchoring member may be integrally molded and formed by a single molding and forming process, such as by molding and forming the suture-anchoring member by injecting fluid plastic into a mold, allowing the plastic to cool, harden, and set, and then removing the mold. Alternatively, the pressure-resisting member, such as a suture-anchoring member, may be integrally formed with the lead such as by fixing and securing the pressure-resisting member to the lead body, such as through a secure fixed connection (for example, a snap fit or interference fit), adhesives, bonding, and/or the like. In such an embodiment, the pressure-resisting member, such as the suture-anchoring member, separately secures and fixes to the lead body without the need of a suture-tie. While the suture-anchoring member is configured to receive a suture tie in order to secure the lead body to patient tissue, the suture tie itself does not securely fix the suture-anchoring member to the lead body. As such, separate and distinct suture sleeves are unnecessary to securely suture the leads to patient tissue.

Figure 1:
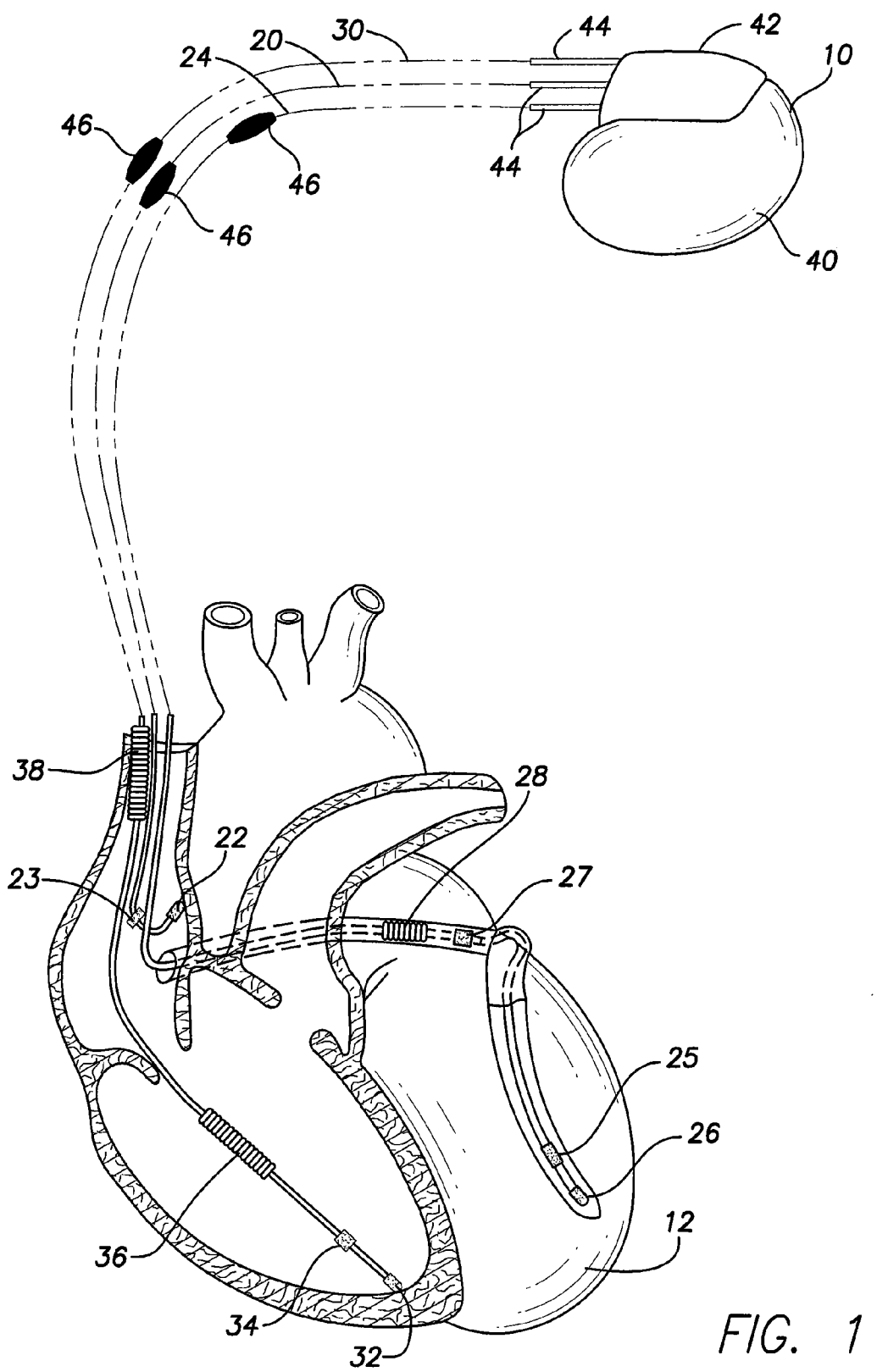
FIG. 1 illustrates an implantable medical device (IMD) in electrical communication with three leads implanted into a patient's heart, according to an embodiment of the present disclosure.

FIG. 1 illustrates an IMD 10 in electrical communication with three leads 20, 24, and 30 implanted into a patient's heart 12, according to an embodiment of the present disclosure. The leads 20, 24, and 30 may be configured to deliver multi-chamber stimulation and/or shock therapy, for example. To sense atrial cardiac signals and to provide right atrial chamber stimulation therapy, the IMD 10 is coupled to an implantable right atrial lead 20 including at least one atrial tip electrode 22 that typically is implanted in the patient's right atrial appendage. The right atrial lead 20 may also include an atrial ring electrode 23 to allow bipolar stimulation or sensing in combination with the atrial tip electrode 22.

To sense the left atrial and left ventricular cardiac signals and to provide left-chamber stimulation therapy, the IMD 10 may be coupled to a lead 24 designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the lead 24 is designed to: receive atrial and/or ventricular cardiac signals; deliver left ventricular pacing therapy using at least one left ventricular tip electrode 26 for unipolar configurations or in combination with left ventricular ring electrode 25 for bipolar configurations; deliver left atrial pacing therapy using at least one left atrial ring electrode 27 as well as shocking therapy using at least one left atrial coil electrode 28.

The IMD 10 is also shown in electrical communication with the patient's heart 12 by way of an implantable right ventricular lead 30 including a right ventricular (RV) tip electrode 32, a right ventricular ring electrode 34, a right ventricular coil electrode 36, a superior vena cava (SVC) coil electrode 38, and so on. Typically, the right ventricular lead 30 is inserted transvenously into the heart 12 so as to place the right ventricular tip electrode 32 in the right ventricular apex such that the RV coil electrode 36 is positioned in the right ventricle and the SVC coil electrode 38 is positioned in the right atrium and/or superior vena cava. Accordingly, the right ventricular lead 30 is capable of receiving cardiac signals, and delivering stimulation in the form of pacing and shock therapy to the right ventricle.

The IMD may be one of various types of implantable devices, such as, for example, an implantable pacemaker, implantable cardioverter-defibrillator ("ICD"), neurostimulator, electrophysiology ("EP") mapping and radio frequency ("RF") ablation system, or the like.

The IMD 10 may include a housing or can 40 that houses the electrical components of the IMD 10. The IMD 10 may also include a header 42 secured to the can 40. The header 42 is configured to receive lead connectors 44 of the leads 20, 24, and 30.

Each lead 20, 24, and 30 may include an integrally-formed pressure-resisting member, such as a suture-anchoring member 46, formed on an outer surface thereof or within the lead 20, 24, and 30. The suture-anchoring member 46 resists the pressure exerted by suture ties. As such, the suture-anchoring member resists squeezing and slipping pressure that may be exerted by one or more suture ties. As shown in FIG. 1, the suture-anchoring members 46 are shown as simplified features. Additional suture-anchoring members 46 may be formed on each lead 20, 24, and 30. For example, the suture-anchoring members 46 may extend over an entire length of the leads 20, 24, and 30. In at least one embodiment, the suture-anchoring members 46 may be regularly spaced from one another on a particular lead 20, 24, or 30. In at least another embodiment, the entire length of each lead 20, 24, and 30 may have an outer surface formed as a suture-anchoring member 46. Alternatively, the suture-anchoring members 46 may be formed between the lead connectors 44 and a middle, for example, of each lead 20, 24, and 30. Optionally, the suture-anchoring members 46 may extend to a point on each lead that would be outside of patient vasculature, such as veins or arteries. For example, the suture-anchoring members 46 may be formed at areas of the leads 20, 24, and 30 that would be outside of patient vasculature. Overall, the suture-anchoring members 46 may be formed at any area of the leads 20, 24, and 30 that may be sutured to patient tissue.

The suture-anchoring members 46 may include defined areas, boundaries, features, or the like that are configured to accept and/or retain one or more sutures. Each suture may be a stitch used to secure a suture-anchoring member 46 to patient tissue. The sutures may be of various known types, such as apposition, approximation, buried, catgut, cobblers, figure-of-eight, or various other types of sutures. The suture-anchoring members 46 may include raised areas, bumps, tabs, grooves, notches, embossments, raised walls, hooks, clasps, and/or the like configured to allow suture material to be securely wound and tied thereto. Additionally, the suture-anchoring members 46 may be defined by thicker areas of an insulating jacket of the lead. The thicker areas may be configured to protect the internal conductors from being compressed by the force of the suture ties. In general, the suture-anchoring members 46 may provide features on exterior surfaces of the leads 20, 24, and 30 for suture material to nest and positively engage and immobilize or anchor the lead with respect to patient anatomy.

While FIG. 1 shows three leads 20, 24, and 30, more or less leads may be used. Further, embodiments of the present disclosure may be used with various other IMDs that may have leads configured to provide therapy to organs other than the heart. For example, embodiments of the present disclosure may be used with neurostimulation devices having leads that connect to nerve endings, the spine, brain, and/or the like. Additionally, embodiments of the present disclosure may be used with any medical device, whether implantable or non-implantable, that includes leads that are to be secured to patient tissue.

Figure 2:
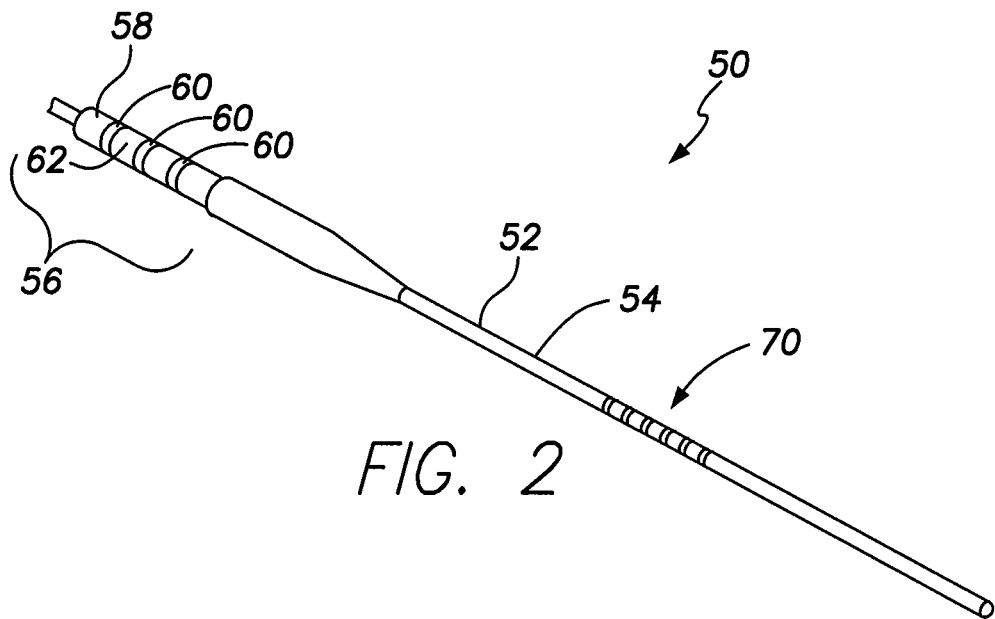
FIG. 2 illustrates an isometric view of a lead, according to an embodiment of the present disclosure.

FIG. 2 illustrates an isometric view of a lead 50, according to an embodiment of the present disclosure. The lead 50 includes a main longitudinal body 52 having an outer insulating jacket 54. A lead connector 56 is located at a proximal end 58 of the lead 50 and is configured to be received and retained within a lead receptacle of a header of a medical device, such as shown in FIG. 1. The lead connector 56 may include one or more lead contacts 60 and seals 62. The lead contacts 60 are configured to electrically contact corresponding electrical terminals within the header, while the seals 62 are configured to prevent the ingress of bodily fluids into the lead receptacle. As shown, the insulating jacket 54 generally does not cover the lead connector 56.

The lead 50 also includes at least one suture-anchoring member 70 that may be integrally molded and formed with the insulating jacket 54 and/or a central core (not shown in FIG. 2) of the lead 50. The insulating jacket 54 and the suture-anchoring member 70 may be integrally molded and formed together, such as through injection molding. For example, the suture-anchoring member 70 may be integrally formed on the insulating jacket through reaction-injection molding (RIM). The insulating jacket 54 and the suture-anchoring member 70 may be formed of various thermoplastic materials. For example, the insulating jacket 54 and the suture-anchoring member 70 may be formed from polyurethane or Optim®, which has been developed by St. Jude Medical, and is a co-polymer insulation created specifically for cardiac lead use. Optim® combines the flexibility and biostability of silicone with the lubricity and durability of polyurethane. Material such as Optim®, polyester, polyether ether ketone (PEEK), and the like are robust and capable of withstanding pressure exerted by suture ties. As such, an insulating jacket 54 formed of such material protects conductors from being compressed or crushed by forces exerted by suture ties.

The suture-anchoring member 70 may be closer to the lead connector 56 than to a distal end of the lead 50 that is configured to be inserted into patient vasculature. For example, the suture-anchoring member 70 may be formed on a proximal portion (which includes the proximal end 58) of the lead 50. In at least one embodiment, the suture-anchoring member 70 may be formed on a proximal quarter, third, or half of the lead 50. While the lead 50 is shown with one suture-anchoring member 70, the lead 50 may include additional suture-anchoring members 70 integrally molded and formed with the insulating jacket 54. Alternatively, longitudinal portions of the lead 50 may be integrally molded and formed with a contiguous suture-anchoring member 70. For example, the longitudinal portions may include a proximal quarter, third, or half, or even an entire length of the lead 50.

Figure 3A:
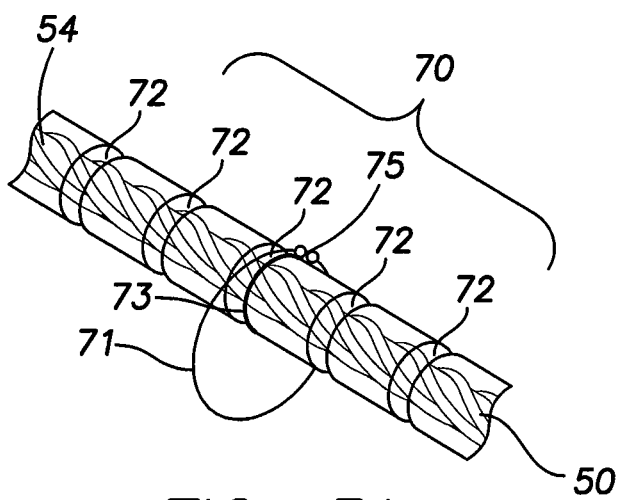
FIG. 3A illustrates an isometric view of a suture-anchoring member integrally formed with a lead, according to an embodiment of the present disclosure.

FIG. 3A illustrates an isometric view of the suture-anchoring member 70 integrally formed with the lead 50, according to an embodiment of the present disclosure. The suture-anchoring member 70 includes features that are configured to retain a portion of a suture 71 therebetween. For example, the suture-anchoring member 70 includes a series of grooves 72 formed in the insulating jacket 54. Each groove 72 is sized and shaped to allow a portion of the suture 71 to nest therein. Each groove 72 may be defined by a constant diameter and be circular in nature. For example, each groove 72 may include a constant radius about a central longitudinal axis of the lead 50. The grooves 72 may be coaxial with respect to a longitudinal axis of the lead 50. The grooves 72 are configured to receive portions of the suture material, which is wound around the suture-anchoring member 70 to anchor the lead to patient tissue. At least portions 73 of the suture material are securely nested within the grooves and tied 75 and knotted around the suture-anchoring member 70.

The grooves 72 may be formed on the insulating jacket 54, which may be formed of a thermoplastic-insulated material, such as Optim®, polyurethane, or the like. For example, the insulating jacket 54, which includes the grooves 72, may be formed through injection-molding, reflow processes, reaction injection molding (RIM), and/or the like.

Figure 3B:
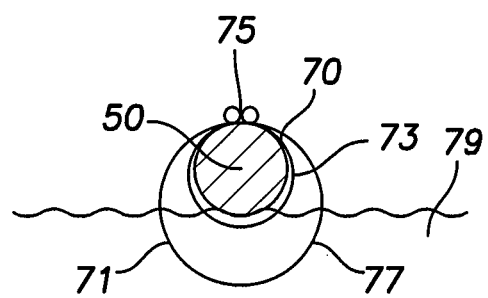
FIG. 3B illustrates an axial cross-sectional view of a lead sutured to patient tissue through a suture-anchoring member, according to an embodiment of the present disclosure.

FIG. 3B illustrates an axial cross-sectional view of the lead 50 sutured to patient tissue 79 through the suture-anchoring member 70, according to an embodiment of the present disclosure. As shown in FIG. 3B, a first portion 73 of the suture 71 may be positioned around the suture-anchoring member 70 and secured with the suture tie 75. A second portion 77 of the suture 71 may be threaded through the tissue 79, around the lead 50, and secured with the suture tie 75.

Figure 4:
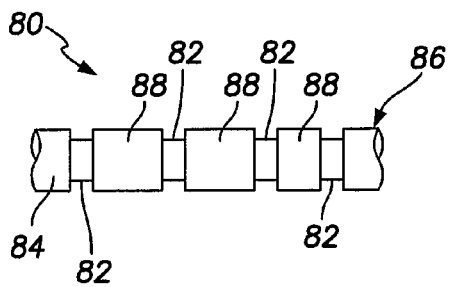
FIG. 4 illustrates a top plan view of a suture-anchoring member, according to an embodiment of the present disclosure.

FIG. 4 illustrates a top plan view of a suture-anchoring member 80, according to an embodiment of the present disclosure. The suture-anchoring member 80 is similar to the suture-anchoring member 70 shown in FIGS. 3A and 3B. The suture-anchoring member 80 includes a plurality of coaxial grooves 82 formed in an insulating jacket 84 of a lead 86. The grooves 82 are circular in axial cross-section. As shown, the grooves 82 may not connect with one another. Instead, each groove 82 may be offset from neighboring grooves by intervening separating walls 88 of the insulating jacket 84. The suture-anchoring member 80 may include more or less grooves 82 than shown.

Figure 5:
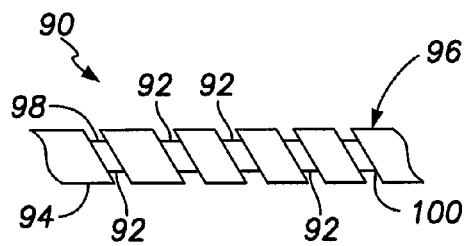
FIG. 5 illustrates a top plan view of a suture-anchoring member, according to an embodiment of the present disclosure.

FIG. 5 illustrates a top plan view of a suture-anchoring member 90, according to an embodiment of the present disclosure. The suture-anchoring member 90 includes a single helical groove 92 that spirals around an insulating jacket 94 of a lead 96. Unlike the separate grooves shown in FIG. 4, the helical groove 92 may be a contiguous groove that extends around the insulating jacket 94 from a first end 98 to a second end 100. The pitch of the helical groove 92 may be tighter or looser than shown.

Figure 6A:
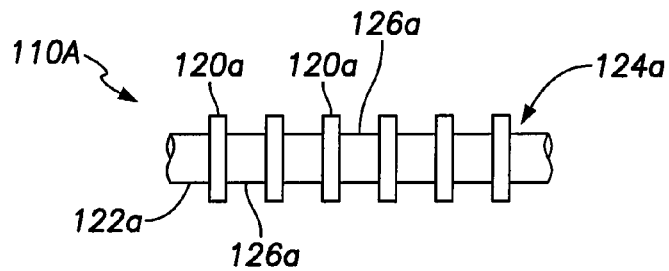
FIG. 6A illustrates a top plan view of a suture-anchoring member, according to an embodiment of the present disclosure.

FIG. 6A illustrates a top plan view of a suture-anchoring member 110a, according to an embodiment of the present disclosure. Instead of grooves, the suture-anchoring member 110a may include a plurality of radially-extending rims 120a that integrally and radially extend from an insulating jacket 122a of a lead 124a. Each rim 120a may be circular or annular in cross-section. The rims 120a may be coaxial and/or concentric with respect to a center longitudinal axis of a lead. The rims 120a define suture-nesting areas 126a therebetween. Each suture-nesting area 126a may be separated from a neighboring suture-nesting area 126a by a rim 120a.

Figure 6B:
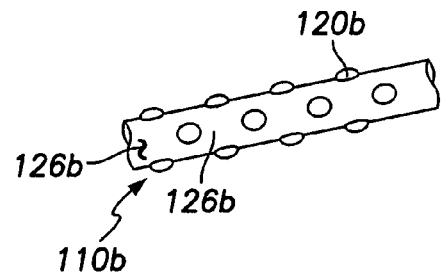
FIG. 6B illustrates an isometric view of a suture-anchoring member, according to an embodiment of the present disclosure.

FIG. 6B illustrates an isometric view of a suture-anchoring member 110b, according to an embodiment of the present disclosure. The suture-anchoring member 110b may include a plurality of protuberances 120b, such as semi-spherical domes, nubs, studs, or the like. As shown, the protuberances 120b may not be circumferentially or radially aligned. A plurality of suture-nesting areas 126b may be defined longitudinally and circumferentially between protuberances 120b.

Figure 6C:
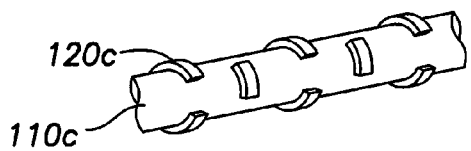
FIG. 6C illustrates an isometric view of a suture-anchoring member, according to an embodiment of the present disclosure.

FIG. 6C illustrates an isometric view of a suture-anchoring member 110c, according to an embodiment of the present disclosure. The suture-anchoring member 110c may include a plurality of protuberances 120c, which may or may not be longitudinally or circumferentially aligned with one another, that may be shaped as spiral-curved rib sections.

Figure 6D:
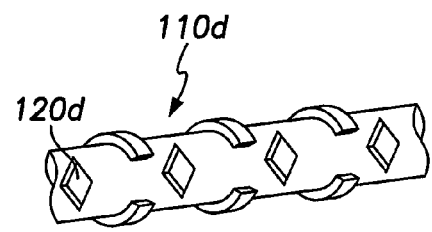
FIG. 6D illustrates an isometric view of a suture-anchoring member, according to an embodiment of the present disclosure.

FIG. 6D illustrates an isometric view of a suture-anchoring member 110d, according to an embodiment of the present disclosure. The suture-anchoring member 110d may include a plurality of protuberances 120d, which may or may not be longitudinally or circumferentially aligned with one another, that may be diamond-shaped, for example.

Referring to FIGS. 6A-6D, the suture-anchoring members may include various features that are sized and shaped to retain portions of a suture. The features may or may not be longitudinally, circumferentially or radially aligned with one another. As shown in FIGS. 6B-6D, for example, the suture-anchoring members may include various types of protuberances defining suture-nesting areas therebetween. The suture-nesting areas may define a circuitous path for suture material to nest.

Figure 7:
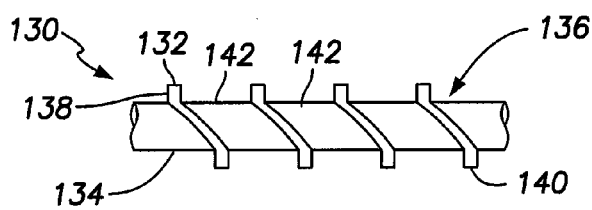
FIG. 7 illustrates a top plan view of a suture-anchoring member, according to an embodiment of the present disclosure.

FIG. 7 illustrates a top plan view of a suture-anchoring member 130, according to an embodiment of the present disclosure. The suture-anchoring member 130 includes a helical rim 132 that spirals around an insulating jacket 134 of a lead 136. The helical rim 132 may be a single, contiguous upstanding wall that extends from a first end 138 to a second end 140. A single helical suture nesting area 142 also spirals around the insulating jacket 134 between portions of the helical rim 132. The pitch of the helical rim 132 may be tighter or looser than shown.

Figure 8:
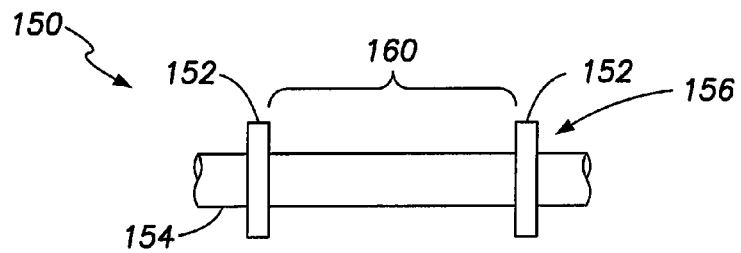
FIG. 8 illustrates a top plan view of a suture-anchoring member, according to an embodiment of the present disclosure.

FIG. 8 illustrates a top plan view of a suture-anchoring member 150, according to an embodiment of the present disclosure. The suture-anchoring member 150 may include opposed rims 152 radially extending from an insulating jacket 154 of a lead 156. The opposed rims 152 may define a suture-retention area 160 therebetween. Suture material may be wound and tied within the suture-retention area 160. The opposed rims 152 prevent the suture material from sliding past the rims 152.

Figure 9:
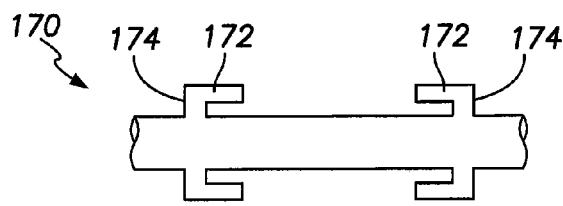
FIG. 9 illustrates a top plan view of a suture-anchoring member, according to an embodiment of the present disclosure.

FIG. 9 illustrates a top plan view of a suture-anchoring member 170, according to an embodiment of the present disclosure. The suture-anchoring member 170 is similar to the suture-anchoring member 150 shown in FIG. 8, except hook members 172 may perpendicularly extend from each rim 174. Opposed hook members 172 are directed toward one another, and are configured to ensure that the suture material remains within the suture-retention area 180. The hook members 172 may be hooks, barbs, clasps, tabs, or the like. Any of the embodiments described above may include hook members, such as the hook members 172. For example, hook members may extend over the grooves 82 shown in FIG. 4.

Figure 10:
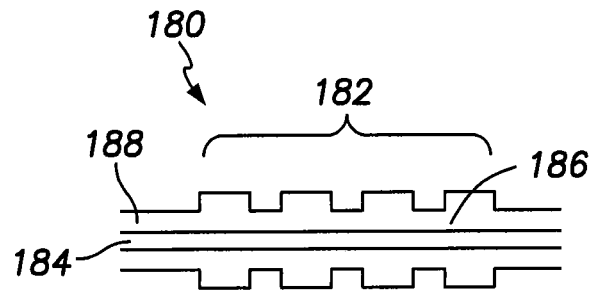
FIG. 10 illustrates a transverse cross-sectional view of an insulating jacket, according to an embodiment of the present disclosure.

FIG. 10 illustrates a transverse cross-sectional view of an insulating jacket 180, according to an embodiment of the present disclosure. The insulating jacket 180 includes a suture-anchoring member 182, such as any of those described above. A channel 184 extends through the insulating jacket 180. As shown in FIG. 10, the suture-anchoring member 182 may have a thicker internal wall portion 186 than the other portions 188 of the insulating jacket 180. The thicker internal wall portion 186 provides additional strength and robustness to the insulating jacket 180, thereby providing further protection against compression or crushing. While the suture-anchoring member 182 is shown with grooves, the suture-anchoring member 182 may or may not include additional features than the thickened internal wall portion 186. For example, an outer surface of the thickened wall portion 186 may simply be a smooth surface.

The insulating jackets described above and shown with respect to FIGS. 2-10 may be formed of a thermoplastic-insulated material, such as Optim®, polyurethane, or the like. For example, the insulating jackets may be formed through injection-molding, reflow processes, reaction injection molding (RIM), and/or the like. Molds formed of thermoset elastomer silicone rubber may be used to form the insulating jackets. When the molds are heated, the insulating jacket material contained therein softens and flows, thereby taking the shape of the internal mold form. After cooling, the mold may then be slid off of the insulating jacket. Any features, such as the suture-anchoring members described above, that may be molded into the silicone rubber mold may be incorporated into the insulating jacket through the reflow process. Optionally, the insulating jackets and features may be molded directly along the underlying lead components through insert molding. Further, reflow processes may be used to vary the thickness of the insulating jackets, such as at areas of the suture-anchoring members.

Figure 11:
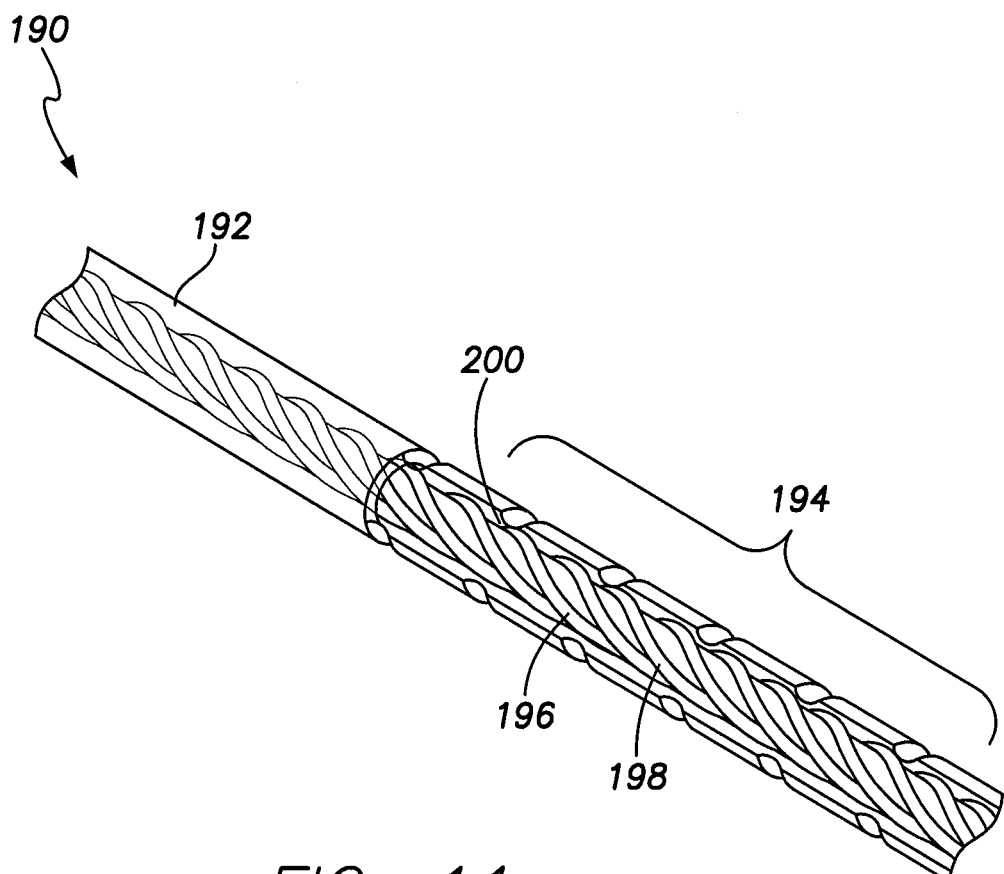
FIG. 11 illustrates an isometric internal view of a lead, according to an embodiment of the present disclosure.

FIG. 11 illustrates an isometric internal view of a lead 190, according to an embodiment of the present disclosure. The lead 190 includes an insulating jacket 192 having a suture-anchoring member 194 integrally molded and formed therewith. The insulating jacket 192 covers one or more conductors 196 and 198 wrapped around a core lumen 200. The conductors 196 and 198 may be helically wrapped around the core lumen 200, such as described in United States Patent Application Publication No. 2010/0228331, entitled "Implantable Medical Lead Having a Body with Helical Cable Conductor Construction and Method of Making Same," which is hereby incorporated by reference in its entirety.

FIG. 12 illustrates an isometric internal view of an insulating jacket 220 of a lead 222, according to an embodiment of the present disclosure. The insulating jacket 220 may include an internal jacket-supporting member 224. For example, the insulating jacket 220 may be injection-molded around the internal jacket-supporting member 224. The jacket-supporting member 224 may underlie a suture-anchoring member 226 or extend past the suture-anchoring member 226. For example, the jacket-supporting member 224 may extend through an entire length of the insulating jacket 220.

The jacket-supporting member 224 may include a tubular mesh 228 that defines an internal channel 230 through which one or more conductors 232 extend. The jacket-supporting member 224 reinforces the insulating jacket 220 at the suture-anchoring member 226. The jacket-supporting member 224 provides reinforcing support to prevent the insulating jacket 220 from being compressed or crushed by suture ties. The jacket-supporting member 224 is configured to provide additional strength and robustness to the insulating jacket 220 to protect against the compressive force of suture ties. The tubular mesh 228 may be formed of various materials, such as polyester, PEEK, or other high strength, flexible, non-conductive materials. Alternatively, the tubular mesh may be formed of flexible metal, such as tin, aluminum, or the like. Optionally, the tubular mesh may be formed of various other materials, such as plastics.

FIG. 13 illustrates an axial cross-sectional view of the insulating jacket 220, according to an embodiment of the present disclosure. As shown, the jacket-supporting member 224 may be contained within the insulating jacket 220 and extend between an outer diameter 231 and an inner diameter 233 of the insulating jacket 220.

FIG. 14 illustrates an isometric view of a jacket-supporting member 240, according to an embodiment of the present disclosure. Instead of a wire mesh, as shown in FIGS. 12 and 13, the jacket-supporting member 240 may include a cylindrical sleeve having an outer circumferential wall 242 defining an internal passage 244. The jacket-supporting member 240 may be formed of various materials, such as flexible metals or plastics.

FIG. 15 illustrates an axial cross-sectional view of an insulating jacket 250, according to an embodiment of the present disclosure. The insulating jacket 250 may include the jacket-supporting member 240. For example, the insulating jacket 250 may be injection-molded around the jacket-supporting member 240. The jacket-supporting member 24 may completely encase the jacket-supporting member 240. Optionally, the insulating jacket 250 may be formed around and/or bonded to an outer surface of the jacket-supporting member 240.

Figure 16:
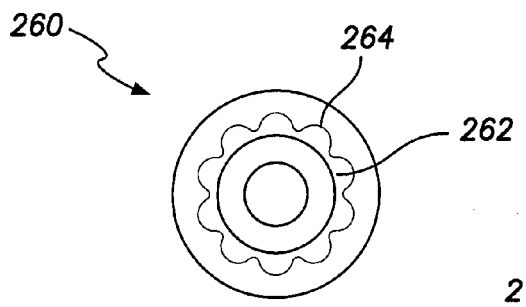
FIG. 16 illustrates an axial cross-sectional view of an insulating jacket, according to an embodiment of the present disclosure.

FIG. 16 illustrates an axial cross-sectional view of an insulating jacket 260, according to an embodiment of the present disclosure. The insulating jacket 260 may be injection-molded around a jacket-supporting member 262, which may include a waved outer circumference 264. The waved outer circumference 264 may provide increased strength and rigidity to the jacket-supporting member 262. While not shown, an internal diameter of the jacket-supporting member 262 may also be waved.

Figure 17:
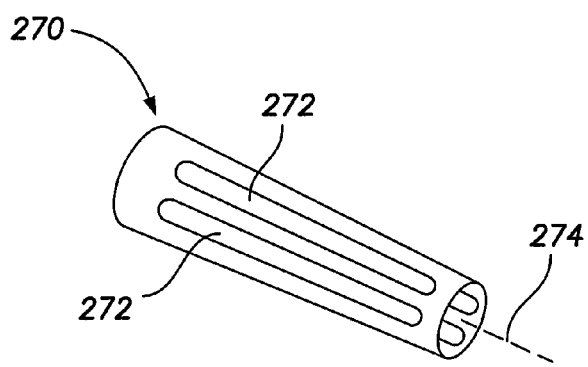
FIG. 17 illustrates an isometric view of a jacket-supporting member, according to an embodiment of the present disclosure.

FIG. 17 illustrates an isometric view of a jacket-supporting member 270, according to an embodiment of the present disclosure. The jacket-supporting member 270 is similar to the jacket-supporting member 240 shown in FIG. 14, except that the jacket-supporting member 270 includes one or more longitudinal channels 272 that are parallel with a longitudinal axis 274 of the jacket-supporting member 270. The longitudinal channels 272 provide additional flexibility to the jacket-supporting member 270.

Figure 18:
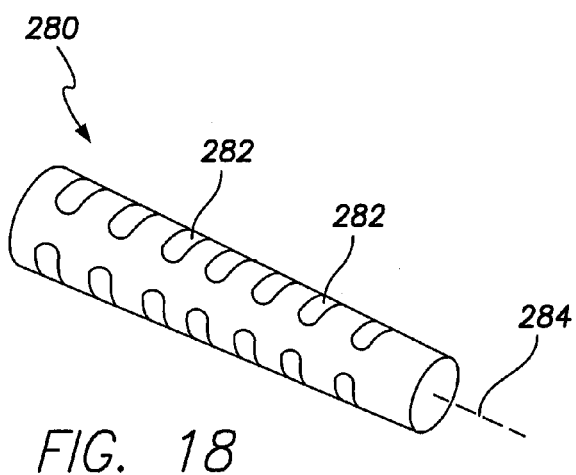
FIG. 18 illustrates an isometric view of a jacket-supporting member, according to an embodiment of the present disclosure.

FIG. 18 illustrates an isometric view of a jacket-supporting member 280, according to an embodiment of the present disclosure. The jacket-supporting member 280 is similar to the jacket-supporting member 240 shown in FIG. 14, except that the jacket-supporting member 280 includes one or more radial channels 282 that radially extend in relation to a central axis 284 of the jacket-supporting member 280.

Figure 19:
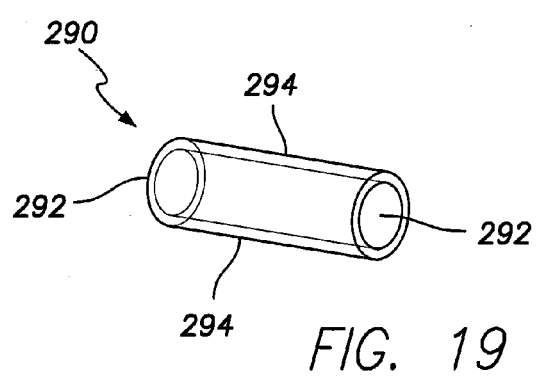
FIG. 19 illustrates an isometric view of a jacket-supporting member, according to an embodiment of the present disclosure.

FIG. 19 illustrates an isometric view of a jacket-supporting member 290, according to an embodiment of the present disclosure. The jacket-supporting member 290 may include opposed end rings 292 connected to one another through one or more longitudinal struts 294.

Referring to FIGS. 12-19, an insulating jacket of a lead may be injection-molded to or around any of the jacket-supporting members shown and described. The jacket-supporting members may be formed of any desired material that provides flexibility, robustness, and/or rigidity to the insulating jacket.

Figure 20:
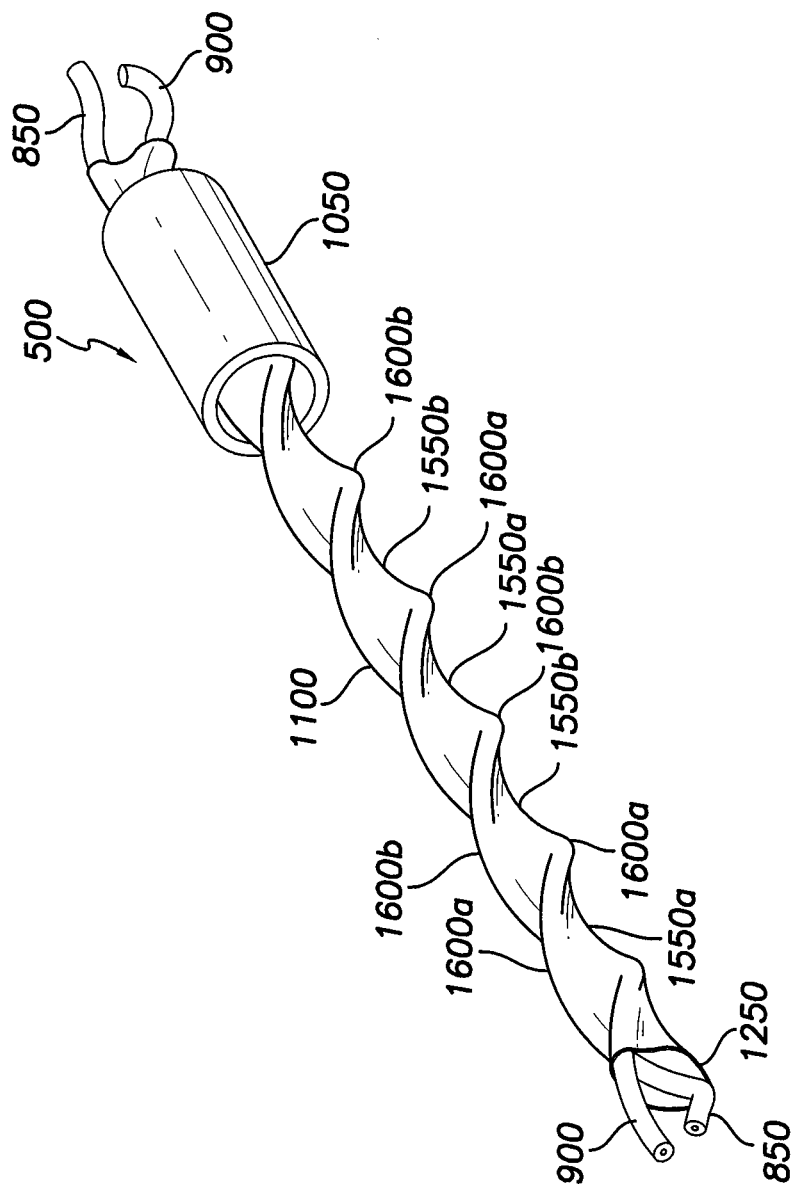
FIG. 20 illustrates an isometric view of a longitudinal segment of a lead with an insulating jacket of the lead mostly hidden to reveal a helical core assembly of the lead, according to an embodiment of the present disclosure.
Figure 23:
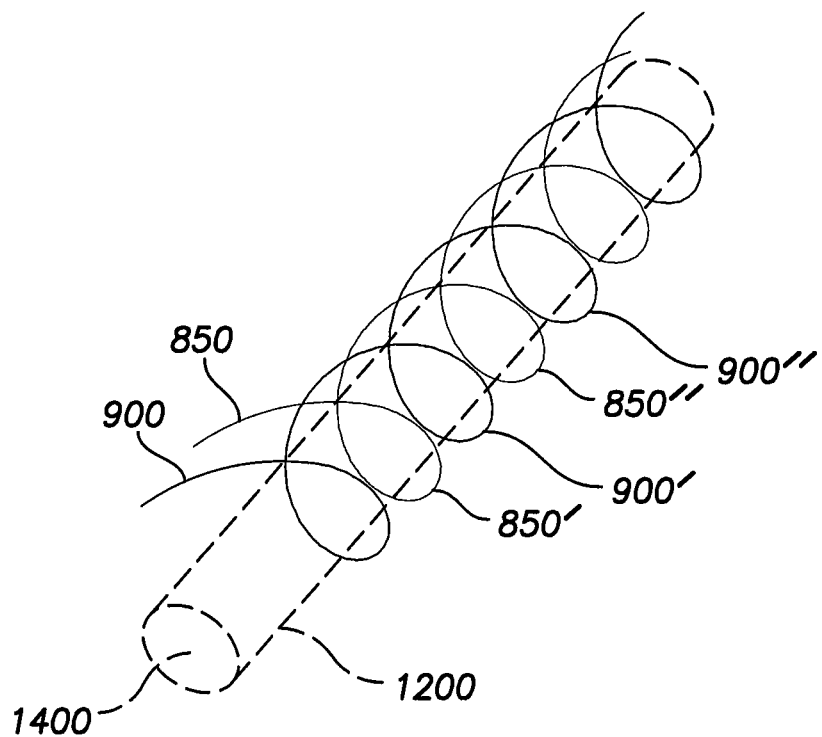
FIG. 23 illustrates an isometric diagrammatic view of an inner liner and helically-routed conductors of a helical core assembly, according to an embodiment of the present disclosure.

FIG. 20 illustrates an isometric view of a longitudinal segment of a lead 500 with an insulating jacket 1050 of the lead 500 mostly hidden to reveal a helical core assembly 1100 of the lead 500, according to an embodiment of the present disclosure. FIG. 21 illustrates a longitudinal side view of the lead 500 of FIG. 20 with the insulating jacket 1050 shown in phantom lines to reveal the helical core assembly 1100, according to an embodiment of the present disclosure. FIG. 22 illustrates a transverse cross-section of the lead 500 as taken along section line 22-22 of FIG. 21, according to an embodiment of the present disclosure. FIG. 23 illustrates an isometric diagrammatic view of an inner liner 1200 and helically-routed conductors 850 and 900 of the helical core assembly 1100, according to an embodiment of the present disclosure.

Referring to FIGS. 20-23, the helical core assembly 1100 forms a central or core portion of the lead 500 and may be enclosed by the outer insulating jacket 1050, which forms an outer circumferential surface 1150 of the lead 500. The insulating jacket 1050 may be formed of silicone rubber, silicone rubber-polyurethane-copolymer ("SPC"), polyurethane, Optim®, and/or the like. While not shown, the insulating jacket 1050 may also include one or more suture-anchoring members, such as any of those described above with respect to FIGS. 1-19.

As illustrated in FIG. 22, in at least one embodiment, the helical core assembly 1100 includes an inner liner 1200, a pair of conductors 850, 900, and a core jacket 1250. The inner liner 1200 includes inner and outer circumferential surfaces 1300 and 1350. The inner circumferential surface 1300 of the inner liner 1200 may define a lumen 1400, which may serve as the central lumen of the lead 500 and through which guidewires and stylets may be extended during the implantation of the lead 500. In at least one embodiment, the inner liner 1200 may be formed of a polymer material such as ethylene tetrafluoroethylene ("ETFE"), polytetrafluoroethylene ("PTFE"), and the like. Alternatively, the inner liner 1200 may be formed of a helical coil conductor.

In at least one embodiment, the two conductors 850 and 900 are located outside the inner liner 1200 adjacent to the outer circumferential surface 1350 of the inner liner 1200. The two conductors 850 and 900 may be evenly radially spaced from each other about the outer circumferential surface 1350 of the inner liner 1200. The conductors 850 and 900 have electrically conductive cores 850a and 900a, respectively, and may or may not have electrical insulation jackets 850b and 900b of their own. Where the conductors 850 and 900 have insulation jackets 850b and 900b, respectively, the insulation jackets 850b and 900b may be formed of a polymer material such as ETFE, PTFE, and the like. The electrically conductive cores 850a and 900a may be multi-wire or multi-filar cores or solid single wire cores.

The helical core assembly 1100 may have two conductors 850 and 900 that are evenly radially spaced apart from each other about the inner liner 120. However, in other embodiments, the conductors 850 and 900 may have other arrangements.

As shown in FIGS. 20, 21, and 23, in particular, the conductors 850 and 900 longitudinally extend along the outer circumferential surface 1350 of the inner liner 1200 in a helical wind. As shown in FIG. 23, in particular, in one embodiment, the adjacent coils 850' and 850" of a specific conductor 850 may not abut against each other. Also, in some embodiments where the multiple conductors 850 and 900 are radially spaced apart from each other about the outer circumferential surface 1350 of the inner liner 1200, the coils 850' and 850" of a first conductor 850 may not abut against the corresponding adjacent coils 900' and 900" of a second conductor 900.

As best understood from FIGS. 20 and 21, in at least one embodiment, the pitch of the helically-routed conductors 850 and 900 is great enough so that the overall length of the helically-routed conductors 850 and 900 if placed in a straight non-helical condition may not be substantially greater than the overall length of a straight-routed conductor for the same length of lead. In at least one embodiment, the pitch of the helically-routed conductors 850 and 900 may be between approximately 0.05" and approximately 0.3".

As shown in FIG. 22, the core jacket 1250 may include an inner surface 1450 and an outer surface 1500. The core jacket 1250 extends about the conductors 850 and 900 and the inner liner 1200, thereby enclosing the inner liner 1200 and the conductors 850 and 900 within the core jacket 1250.

The core jacket 1250 may snugly fit about the inner liner 1200 and the conductors 850 and 900 such that the inner surface 1450 of the core jacket 1250 extends along and generally conforms to portions of the outer circumferential surface 1350 of the inner liner 1200 and the outer surfaces of the conductors 850 and 900 (for example, the outer surfaces of the insulation jackets 850b and 900b, where present). Where there are two conductors 850 and 900, the resulting transverse cross-section of the helical core assembly 1100 may have a first diameter D1, which aligns with a first axis A extending through the center points of the conductors 850 and 900 and the lumen 1400, that is substantially longer than a second diameter D2, which aligns with a second axis B that is generally perpendicular to the first axis A.

As shown in FIGS. 21 and 22, on account of the helical routing of the conductors 850 and 900 about the inner liner 1200 and the general conforming of the core jacket 1250, the outer surface 1500 of the core jacket 1250 may be helical, defining helically extending troughs 1550a and 1550b separated by helically extending ridges 1600a and 1600b. Where the helical core assembly 1100 includes two helically-routed conductors 850 and 900 and the core jacket 1250 generally conforms to the conductors 850 and 900 and inner liner 1200, the outer surface 1500 of the core jacket 1250 may have a pair of troughs 1550a and 1550b and a pair of ridges 1600a and 1600b. Where the helical core assembly 1100 includes one, three, four, five and so forth helically-routed conductors and the core jacket 1250 generally conforms to the conductors and inner liner 1200, the outer surface 1500 of the core jacket 1250 may have respectively one, three, four, five and so forth troughs and one, three, four, five and so forth ridges.

Referring to FIGS. 20-23, the location and routing of each helically extending ridge 1600a and 1600b corresponds with and generally matches the location and routing of a specific helically-routed conductor 850 and 900. The location and routing of each helically extending through 1550a and 1550b corresponds with and generally matches the location of a space centered between a pair of helically-routed conductors 850 and 900. The helical configuration of the conductors 850 and 900 serves to effectively decouple the conductors 850 and 900 from the normal strains of the lead 500 in bending, even if the conductors 850 and 900 are potted in the material of the insulating jacket 1050.

In some embodiments, the pitch may be small, medium, or large such that the overall length of the conductors 850 and 900 exceeds the overall length of straight-routed conductors to a greater or lesser extent. Additionally, the pitch of particular conductor may vary as it extends along the lead 500.

As indicated in FIG. 23, in particular, in at least one embodiment, the helical core assembly 1100 may be encased or embedded in the material of the insulating jacket 1050 of the lead 500. The outer circumferential surface 1150 of the insulating jacket 1050 may form the outer circumferential surface 1150 of the lead 500. The outer jacket 1050 may be such that it in-fills the voids between the lead body outer circumferential surface 1150 and the core jacket outer surface 1500 in the vicinity of the troughs 1550a and 1550b. The result is a lead 500 with an outer circumferential surface 1150 having a generally circular shape in transverse cross-section and generally uniform diameter along its length, despite the helical core assembly 1100 having a transverse cross-section that may be semi-elliptical.

Embodiments of the present disclosure may be used with respect to helically-routed conductors. It has been found that helically-routed conductors provide an inherently robust lead construction that is able to withstand pressures exerted by suture ties. For example, any of the suture-anchoring members described above may be integrally molded and formed with the insulating jacket 1050 shown in FIGS. 20-22. Helically-routed conductors are further described in United States Patent Application Publication No. 2010/0228331, entitled "Implantable Medical Lead Having a Body with Helical Cable Conductor Construction and Method of Making Same," which was previously incorporated by reference in its entirety. Alternatively, embodiments of the present disclosure may be used with various other conductor configurations, such as linear, coaxial, stacked, and/or the like.

FIG. 24 illustrates an isometric view of a pressure-resisting member, such as a lead-strengthening member 401, integrally formed with a lead 400, according to an embodiment of the present disclosure. FIG. 25 illustrates an isometric partial-internal view of the lead-strengthening member 401 integrally formed with the lead 400. Referring to FIGS. 24 and 25, the lead 400 may include a central core 402, such as a central tube formed of silicone, and a lead-strengthening member 400 wrapped around the central core 402. An insulating jacket 403 (shown in FIG. 25), which may be formed of Optim®, for example, wraps around the lead-strengthening member 400 and the central core 402.

The central core 402 may include a central channel (hidden from view) that retains one or more conductors, such as any of those described above. For example, the central core 402 may retain conductors as shown and described with respect to FIGS. 20-23.

The lead-strengthening member 400 may include a mesh, lattice, or other support frame structure that wraps around the central core 402 in a braided pattern. The lead-strengthening member 400 may be formed of a fluoropolymer. In general, the lead-strengthening member 400 may be formed of various materials, such as polyether ether ketone (PEEK), and the like that are robust and capable of withstanding abrasive and/or crushing forces exerted by implantable devices, other leads, patient anatomy, and the like. The lead-strengthening member 400 may include one or more fibers 404 and 406 that wrap around the central core 402. The fiber 404 may spirally wrap around the central core 402 in a spiral direction 408, while the fiber 406 may wrap around the central core 402 in a spiral direction 410 that is opposite the spiral direction 408. Accordingly, the spiral-wound fibers 404 and 406 may form a lattice that includes multiple intersections 412 and openings 414.

The lead-strengthening member 400 may be formed by spiral winding each of the fibers 404 and 406 around the central core 402. For example, the fibers 404 and 406 may be wound and bonded to the central core 402. Alternatively, the central core 402 may include channels into which the fibers are retained. Also, alternatively, the fibers 404 and 406 may be adhesively secured to the central core 402.

Optionally, the fibers 404 and 406 may be integrally molded and formed with the central core 402. For example, a single mold may be used to receive injection-molded plastic. After the plastic cools, hardens, and sets, portions of the plastic may be removed, such as through cutting, scoring, or the like, to form the openings 414, thereby defining the intersections 412.

After the fibers 404 and 406 are formed with respect to the central core 402, the insulating jacket 403 may be integrally formed over the fibers 404 and 406. For example, the insulating jacket 403 may be wrapped around the fibers 404 and 406, thereby compressively sandwiching the fibers 404 and 406 between the insulating jacket 403 and the central core 402. Alternatively, the insulating jacket 403 may be formed through injection-molding material, such as Optim®, around the fibers 404 and 406 and the central core 402. Also, alternatively, the insulating jacket 403 may be integrally molded and formed with the central core 402 and the lead-strengthening member 401.

The lead-strengthening member 401 provides an abrasion-resistant barrier between the central core 402 and the insulating jacket 403. Accordingly, even if the insulating jacket 403 is penetrated through an abrasive force, the lead-strengthening member 401 prevents the central core 402 from abrasion. Further, the openings 414 provide flexibility to the lead-strengthening member 401. As such, while the lead-strengthening member 401 provides a pressure-resisting member, the lead-strengthening member 401 is flexible enough to be navigated through patient vasculature without causing damage thereto.

The lead-strengthening member 401 may be perforated, radially-cut material, a mesh, or the like that forms the braided fibers 404 and 406, as described above. The pitch of the spiral of each of the fibers 404 and 406 may be greater or less than shown in FIGS. 24 and 25. More or less than two-fibers may be used to form the lead-strengthening member 401. Further, while the lead-strengthening member 401 is described as having spiral-wound fibers 404 and 406, the fibers 404 and 406 may alternatively extend along and/or wrap around portions of the central core 402 in various other orientations. For example, the lead-strengthening member 401 may include multiple fibers that linearly extend over portions of the central core 402.

The lead-strengthening member 401 may be formed over various lengths of the lead 400. For example, the lead-strengthening member 401 may be formed over an entire length of the lead 400, or through one or more fractional portions of the lead 400. As another example, the lead-strengthening member 401 may be formed under portions of suture-anchoring members, such as any of those described above.

Figure 26:
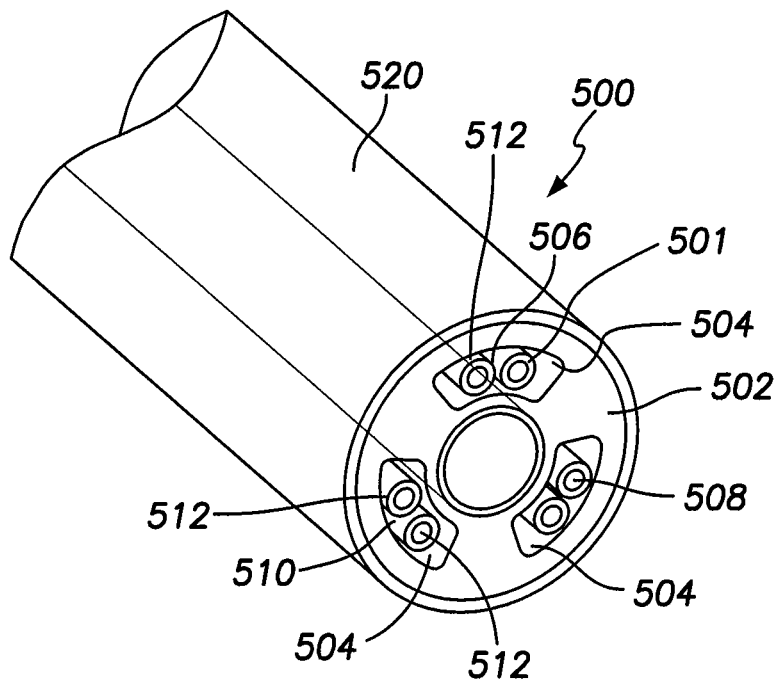
FIG. 26 illustrates an isometric partial-internal view of a lead-strengthening member integrally formed with a lead, according to an embodiment of the present disclosure.

FIG. 26 illustrates an isometric partial-internal view of a lead-strengthening member 501 integrally formed with a lead 500, according to an embodiment of the present disclosure. The lead 500 includes a central core 502 having passages 504 that retain fibers 506, 508, and 510 of the lead-strengthening member 501. An insulating jacket 520 wraps around the central core 502, as described above.

The fibers 506, 508, and 510 may wrap around the central core 502 within the passages 504 in a spiral pattern, linear pattern, or the like, such as described above. Each fiber 506, 508, and 510 may include parallel tubes 512. For example, each fiber 506, 508, and 510 may include two parallel, hollow tubes 512, which may or may not be connected to one another. Alternatively, each fiber 506, 508, and 510 may include more or less tubes 512 than shown.

Figure 27:
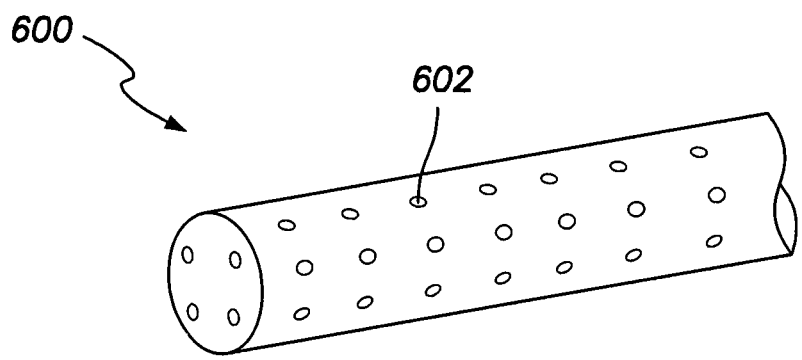
FIG. 27 illustrates an isometric view of a lead-strengthening member, according to an embodiment of the present disclosure.

FIG. 27 illustrates an isometric view of a lead-strengthening member 600, according to an embodiment of the present disclosure. Instead of individual fibers that are configured to wrap around a central core, the lead-strengthening member 600 may include a sleeve 602 having a plurality of perforations 602 formed therethrough. The perforations 602 may be holes, slits, or other such openings formed through the sleeve 602. The perforations 602 may be various sizes and shapes, such as circular, diamond, triangular, square, crescent, and/or the like. The perforations 602 may be formed in a spiral pattern around the sleeve, or various other patterns, such as concentric rings of perforations. More or less perforations 602 than shown may be used. Increased perforations provide increased flexibility. A manufacturer may tailor the number, shape, and pattern of perforations based on a desired flexibility and resistance to abrasion and crushing force, for example.

Referring to FIGS. 24-27, embodiments of the present disclosure provide pressure-resisting members, such as lead-strengthening members, that may be integrally formed with a lead. For example, the lead-strengthening members may be integrally formed and/or molded with a central core and/or an insulating jacket of a lead. The lead-strengthening members resist abrasive and/or crushing forces that may be exerted toward the central cores of leads, such as by implantable devices, other leads, patient anatomy, and the like.

Embodiments of the present disclosure provide a lead having at least one pressure-resisting member, such as a lead-strengthening member and/or a suture-anchoring member. For example, the lead-strengthening member may be used in conjunction with a suture-anchoring member.

As described above, embodiments of the present disclosure provide leads having insulating jackets that may be integrally molded and formed with pressure-resisting members, such as suture-anchoring members configured to allow sutures to be secured and tied thereto, and/or lead-strengthening members. Embodiments of the present disclosure may not use separate and distinct suture sleeves. Instead, the integral suture-anchoring members provide areas, boundaries, and/or features that allow the lead to be directly sutured to patient anatomy.

As noted above, embodiments of the present disclosure may be used with any medical device that includes leads that are configured to be secured to patient anatomy. The medical device may be implantable, such that it is configured to be implanted within patient anatomy, or non-implantable, such that it is configured to be secured on an outside surface of skin of an individual. For example, embodiments of the present disclosure may be used with respect to implantable pacemakers, implantable cardioverter-defibrillators, internal or external neurostimulation devices, Holter monitors, and the like. Embodiments of the present disclosure may be implemented in connection with an implanted or external neurostimulation device such as, but without limitation, the devices described in U.S. Pat. No. 7,983,762, U.S. Pat. No. 7,738,963, U.S. Pat. No. 7,684,866, and U.S. Pat. No. 7,532,936, all of which are incorporated by reference herein in their entireties.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A medical device configured to be secured to an individual, the medical device comprising:
   a housing containing one or more electrical components; and
   one or more leads electrically connected to the housing, wherein each of the one or more leads comprises:
   an insulating jacket that surrounds a central core including one or more conductors, wherein the insulating jacket and central core extend from a proximal portion of each of the one or more leads to a distal portion of each of the one or more leads; and
   at least one pressure-resisting member integrally formed with one or both of the insulating jacket or the central core, wherein the at least one pressure-resisting member is disposed between the proximal and distal portions of the one or more leads, and wherein the at least one pressure-resisting member is configured to resist one or more forces exerted into the central core;

wherein the at least one pressure-resisting member has at least one suture-anchoring member integrally formed with one or both of the insulating jacket or the central core, wherein the at least one suture-anchoring member has at least one feature on an outer surface of the lead that is configured to retain at least a portion of suture material that is configured to securely anchor the one or more leads to tissue of the individual.

2. The medical device of claim 1, wherein the at least one feature comprises one or more grooves formed on an outer surface of the insulating jacket configured to allow the portion of suture material to nest therein.

3. The medical device of claim 2, wherein the one or more grooves comprises coaxial circular grooves.

4. The medical device of claim 2, wherein the one or more grooves comprises a single helical groove that spirals around at least a portion of the insulating jacket.

5. The medical device of claim 1, wherein the at least one feature comprises one or more rims radially extending from an outer surface of the insulating jacket.

6. The medical device of claim 1, wherein the at least one suture-anchoring member comprises one or more of a hook, barb, clasp, or tab.

7. The medical device of claim 1, wherein the at least one suture-anchoring member comprises a thickened wall portion configured to resist compressive force.

8. The medical device of claim 1, wherein the at least one pressure-resisting member comprises at least one lead-strengthening member integrally formed with one or both of the insulating jacket or the central core, wherein the at least one pressure-resisting member is configured to resist abrasive or crushing forces exerted by one or more of the housing, another lead, or patient anatomy.

9. A lead configured to be electrically connected to a medical device configured to be secured to an individual, the lead comprising:

an insulating jacket that surrounds a central core including one or more conductors, wherein the insulating jacket and the central core extend from a proximal portion of each of the one or more leads to a distal portion of each of the one or more leads; and at least one pressure-resisting member integrally formed with one or both of the insulating jacket or the central core, wherein the at least one pressure-resisting member is disposed between the proximal and distal portions of the one or more leads, and wherein the at least one pressure-resisting member is configured to resist one or more forces exerted into the central core;

wherein the at least one pressure-resisting member has at least one suture-anchoring member integrally formed with one or both of the insulating jacket or the central core, wherein the at least one suture-anchoring member has at least one feature on an outer surface of the lead that is configured to retain at least a portion of suture material that is configured to securely anchor the one or more leads to tissue of the individual.

10. The lead of claim 9, wherein the at least one feature comprises one or more grooves formed on an outer surface of the insulating jacket configured to allow the at least a portion of suture material to nest therein.

11. The lead of claim 9, wherein the at least one suture-anchoring member comprises a thickened wall portion configured to resist compressive force.

12. The lead of claim 9, wherein the at least one suture-anchoring member comprises at least one jacket-supporting member contained within or bonded to the insulating jacket.

13. The lead of claim 9, wherein the at least one suture-anchoring member comprises a plurality of regularly-spaced suture-anchoring members regularly spaced over a portion of the insulating jacket.

14. The lead of claim 9, wherein the at least one suture-anchoring member extends over an entire length of the insulating jacket.

15. The lead of claim 9, wherein the at least one pressure-resisting member comprises at least one lead-strengthening member integrally formed with one or both of the insulating jacket or the central core, wherein the at least one pressure-resisting member is configured to resist abrasive or crushing forces exerted by one or more of the medical device, another lead, or patient anatomy.

16. The lead of claim 9, wherein the at least one lead-strengthening member comprises one or more fibers extending along at least a portion of the central core.

17. The lead of claim 16, wherein the one or more fibers comprises at least two fibers spirally-wound around the central core to form a lattice.

* * * * *